United States Patent [19]

LeVahn

[11] Patent Number: 4,930,932

[45] Date of Patent: Jun. 5, 1990

[54] QUICK RELEASE ATTACHMENT MECHANISM

[75] Inventor: Bruce A. LeVahn, New Brighton, Minn.

[73] Assignee: Minnesota Scientific, Inc., West St. Paul, Minn.

[21] Appl. No.: 330,420

[22] Filed: Mar. 29, 1989

[51] Int. Cl.⁵ ............................................. B25G 3/18
[52] U.S. Cl. .................................. 403/325; 403/327; 403/324; 279/76
[58] Field of Search ............... 403/327, 328, 325, 354, 403/241, 324; 279/76, 86, 79

[56] References Cited

U.S. PATENT DOCUMENTS

| | | | |
|---|---|---|---|
| 77,219 | 4/1868 | Rundlett | 279/86 |
| 173,686 | 2/1876 | Starr | 279/76 U X |
| 357,429 | 2/1887 | Walker | 279/76 |
| 601,544 | 3/1898 | Bennett | 403/325 |
| 1,176,205 | 3/1916 | Cutlip | 403/325 |
| 2,450,194 | 9/1948 | Glaser | 128/20 |
| 2,670,731 | 3/1954 | Zoll et al. | 128/20 |
| 2,850,008 | 9/1958 | Resch | 128/20 |
| 3,227,156 | 1/1966 | Gauthier | 128/20 |
| 3,384,078 | 5/1968 | Gauthier | 128/20 |
| 3,604,735 | 9/1971 | Hoffmeister | 279/76 X |
| 4,120,302 | 10/1978 | Ziegler | 128/322 |
| 4,344,420 | 8/1982 | Forder | 128/20 |

Primary Examiner—Andrew V. Kundrat
Attorney, Agent, or Firm—Kinney & Lange

[57] ABSTRACT

A retractor system having a plurality of quick release retractor blades. The retractor system includes a shaft cooperating with the retractor system for positioning a selected one of the quick release retractor blades. The quick release attachment mechanism is distributed between the shaft and the blades, the shaft having a first end thereof adapted for attachment to a selected quick release retractor blade. A pair of grooves extending longitudinally from the first end along opposite sides of the outside of the shaft. A retaining groove grids the shaft spaced from the first end. Each retractor blade has a pair of tongues disposed in a plane and oriented inwardly toward one another. A torsion spring is attached to each blade and a flange extends from the torsion spring through the plane of the tongues. An aperture through the flange is sized and positioned to admit the shaft with the longitudinal grooves engaging the tongues. The torsion spring is flexed upon admission of the shaft such that an edge of the aperture is urged into engagement with the retaining groove when the aperture and the retaining groove are adjacent one another. The retractor blade is released by flexing the torsion spring to remove the edge of the aperture from the retaining groove.

16 Claims, 5 Drawing Sheets

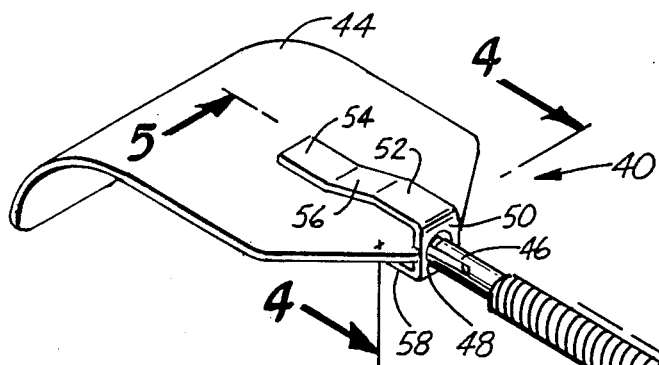
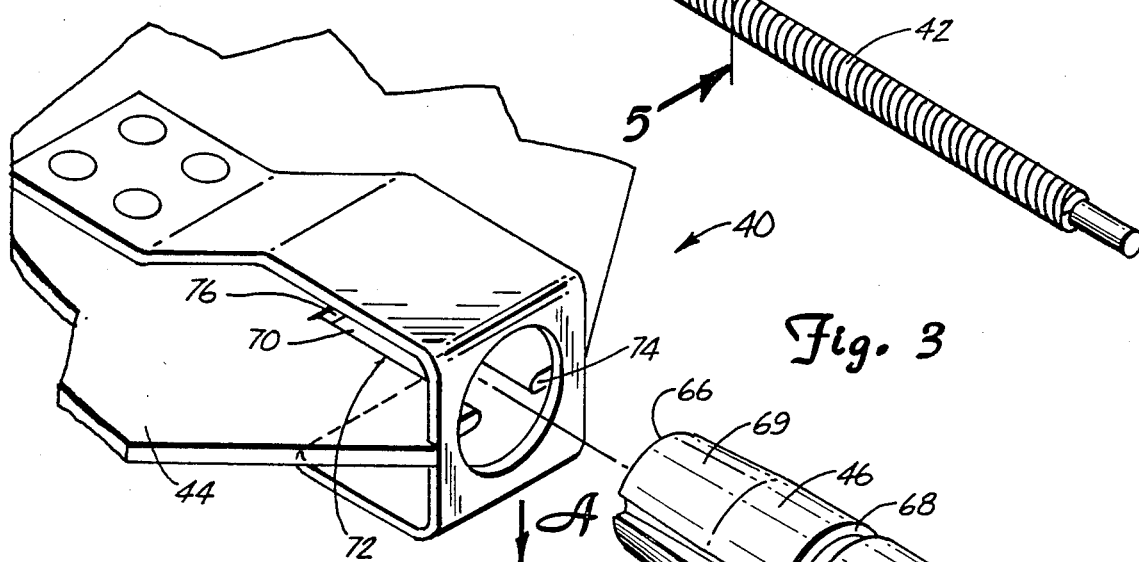
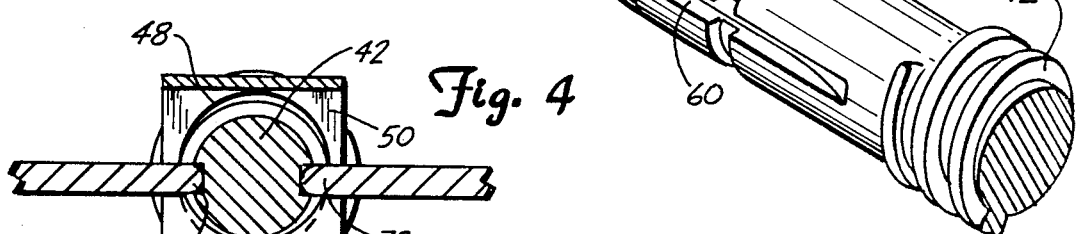
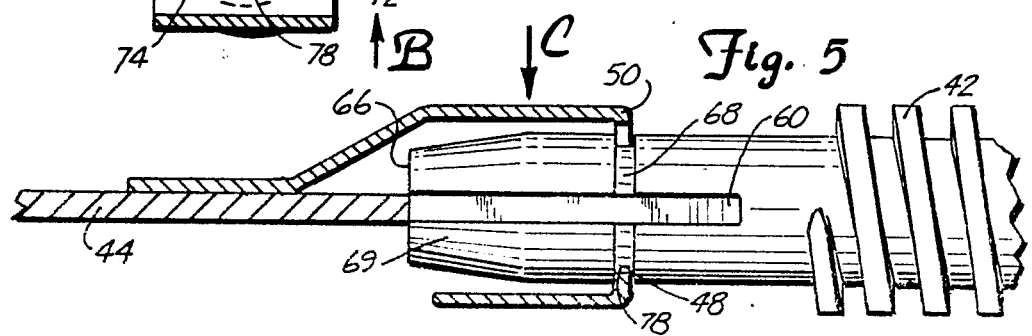

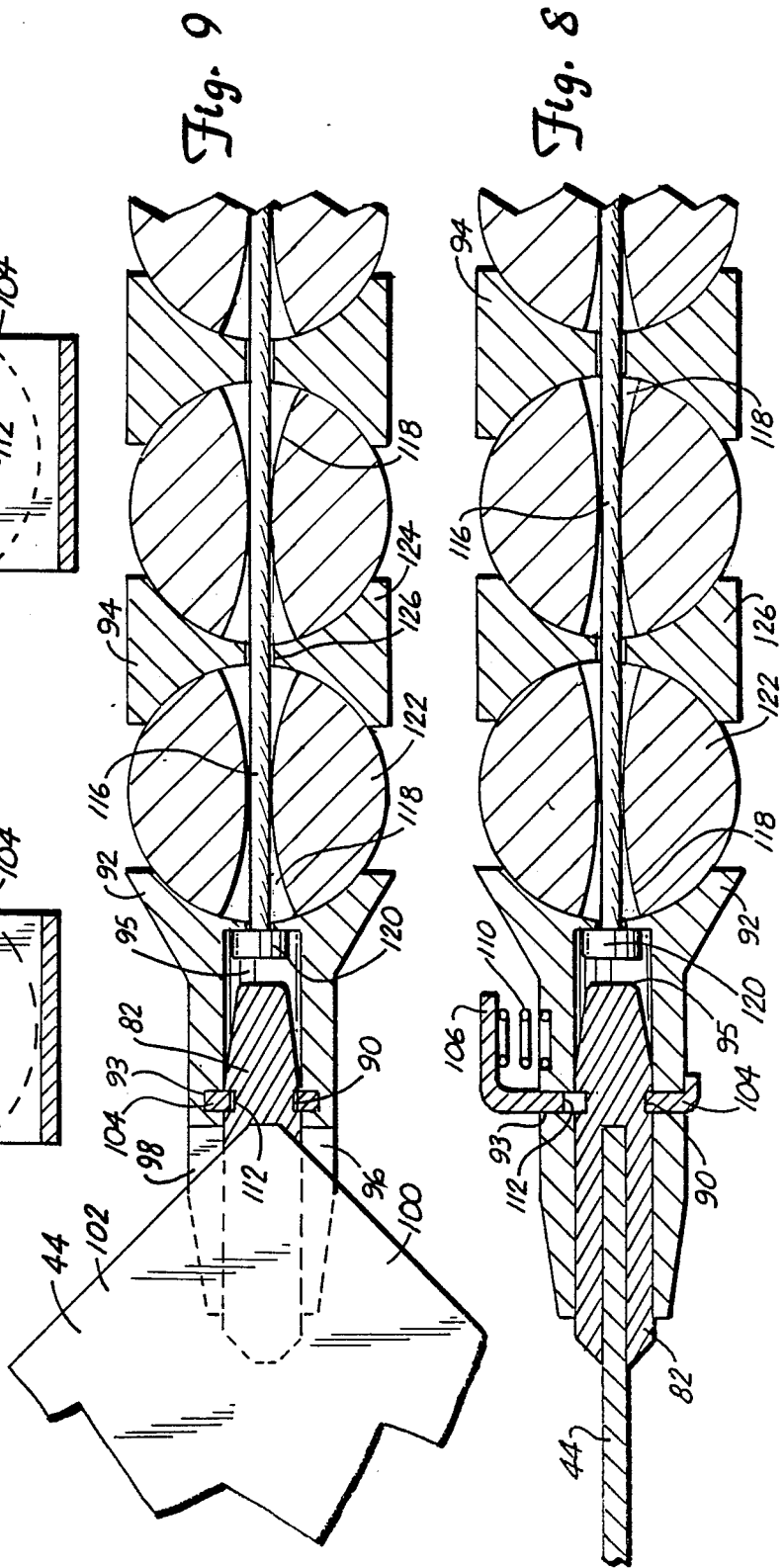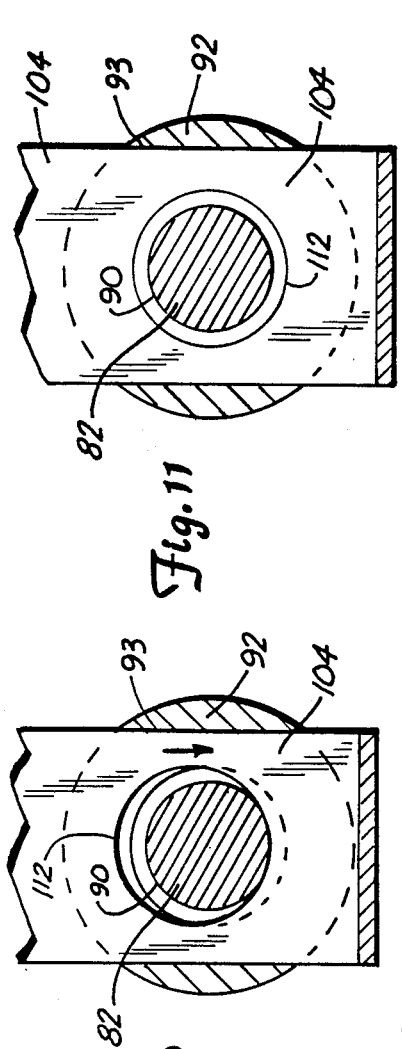

QUICK RELEASE ATTACHMENT MECHANISM

The invention relates to surgical appliances and more particularly to quick release latching of retractor blades into surgical retractor systems.

BACKGROUND OF THE INVENTION

Retractor blades and rakes are mounted to a positioning apparatus including a supporting framework positioned adjacent to the subject undergoing surgery. Types and sizes of blades and rakes used in an operation, and during different stages of one operation, can depend upon a number of factors, including but not limited to, the type of the operation, the particular part of the anatomy operated on, the body weight of the individual operated on, and so forth. It is convenient to be able to change the specific blades and rakes mounted to the positioning apparatus during the course of the operation. At the same time, the positioning apparatus for the retractor blades and rakes should present minimum obstruction to the surgical team's activities, particularly in the area of an incision.

Interchangeable retractor blades are known and have been used in surgery for a number of years. Interchangeable blades, of various lengths, have been applied to abdominal surgery where the body walls of patients vary substantially in thickness. However, in certain retraction systems, the blades and rakes are fixed to the ends of elongated shafts, which are in turn mounted to the support frame. Elongated shafts afford the possibility of locating the supporting framework of the positioning apparatus well clear of the incision. In retractor systems incorporating blades disposed at the ends of shafts and flexible arms, the shafts/arms and blades have been of one-piece construction, and a change of a blade or rake has involved removal of a shaft/arm and replacement with another shaft/arm carrying the desired blade or rake. Where the shaft is of a high precision, threaded type, maintaining an inventory of appropriately sized blades is expensive. However, no suitable technique of replaceable attachment of blades to shafts, affording quick replacement of blades, has been available.

SUMMARY OF THE INVENTION

The invention is directed to an attachment mechanism for use in a retractor system. The attachment mechanism affords selective, quick releasing attachment of one from a plurality of types of retractor tools to a tool positioning portion of the retractor system.

The quick release attachment mechanism is distributed between a retraction tool and the positioning mechanism from which the tool depends in use. The specific distribution of attributes of the mechanism between retraction tool and the means for positioning the tool depends upon the type of tool positioning means used in a given application. Retraction tools are typically positioned at the ends of elongated shafts, or at the ends of flexible arms which can be stiffened by drawing taught an internal cord bringing individual members of the arm into locking engagement with one another.

The elements of the attachment mechanism in either embodiment include, an elongated coupling shaft having a lead end, a latch catch positioned on or with respect to the shaft, a guide adapted to cooperate with the coupling shaft for positioning and orienting the shaft for movement along the longitudinal axis of the shaft, a latch disposed across and substantially perpendicular to the path of orientation and movement of the coupling shaft for engaging latch catch, and a spring for biasing the latch toward a position for catching the latch catch to close the attachment mechanism.

The quick release attachment mechanism of the present invention is closed simply by pressing a tool onto the positioning means. It is opened by grasping tool or positioning means, depending upon which carries the latch and latch biasing spring, to counteract the effect of the spring and release the latch from the latch catch. The permits allow the tool to be slid from the positioning means.

A quick release retractor blade is released by flexing the torsion spring to remove the edge of the aperture from the girding groove. Blades may be easily grasped to slide a blade onto the shaft and off again.

BRIEF DESCRIPTION OF THE DRAWINGS

FIG. 2 is a perspective view of the quick release attachment mechanism for coupling shaft and blade.

FIG. 3 is a perspective view of the quick release attachment mechanism of FIG. 2 with shaft and blade unlatched.

FIG. 4 is a section view taken along section line 4—4 of FIG. 2.

FIG. 5 is a section view taken along section line 5—5 of FIG. 2.

FIG. 8 is a cross-sectional view taken along section line 8—8 in the direction indicated in FIG. 6B.

FIG. 10 is a partial section end view of a latching flange in the latched position.

FIG. 11 is a partial section end view of a latching flange displaced from the latched position.

DETAILED DESCRIPTION OF THE PREFERRED EMBODIMENTS

Figure 1:
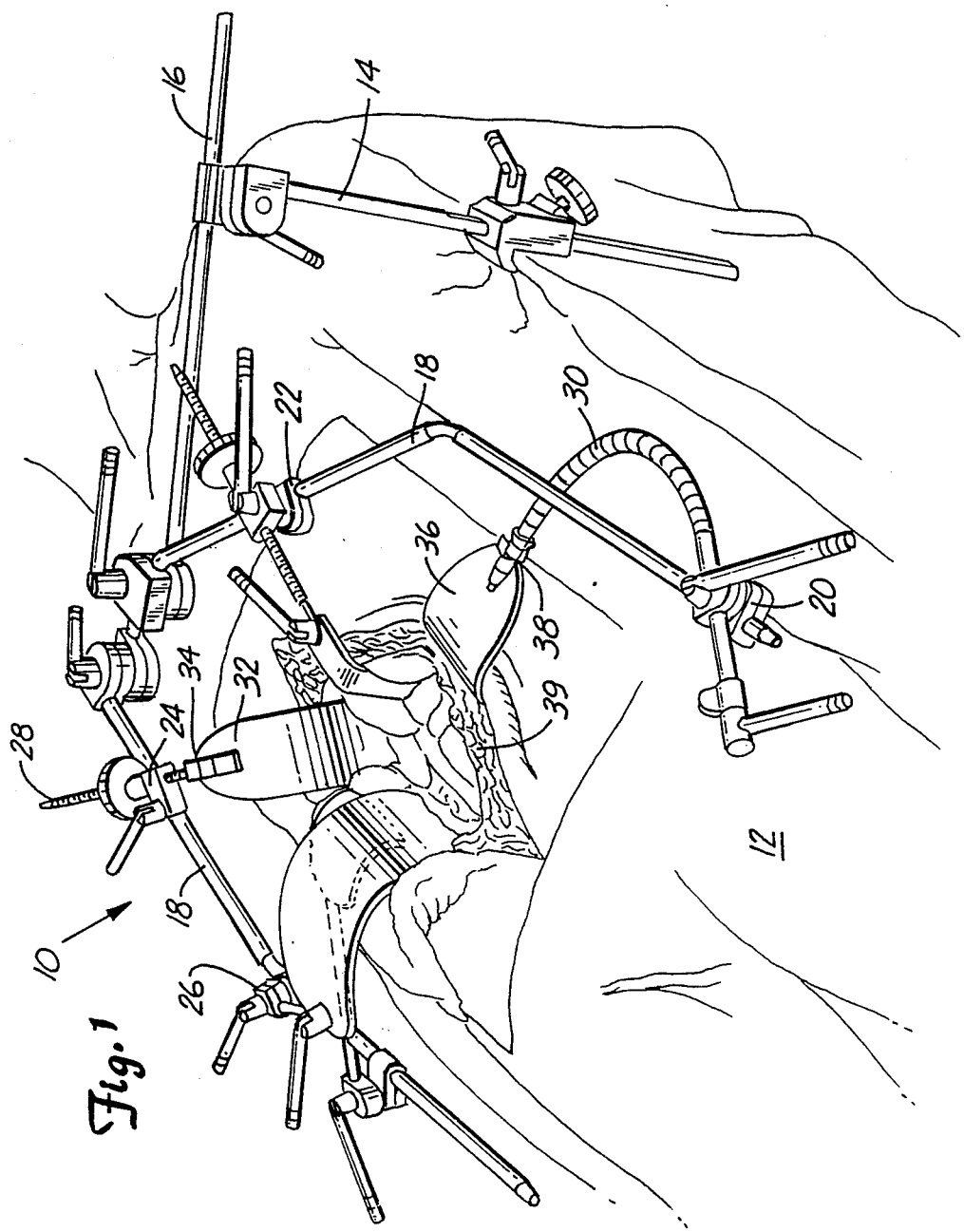
FIG. 1 is a perspective view of a retractor assembly incorporating the quick release attachment mechanism of the present invention.

FIG. 1 illustrates use of a retraction assembly 10 to provide retraction of a surgical incision in a patient 12. A stand 14 is height adjustable and supports a cross arm 16. Cross arm 16 carries a generally U-shaped spreadable support member 18 which brackets the abdominal area of a patient 12 undergoing surgery. Clamps 20, 22, 24 and 26 are positioned around U-shaped support member 18 for carrying a variety of retraction tool positioning members or for directly supporting a retraction tool. The retraction assembly shown is not meant as a recommended combination of positioning members or use of the members shown. Positioning members such as elongated shaft 28 are mounted to clamp 24 and flexible arm 30 is mounted to clamp 20. Elongated shaft 28 is threaded and is useful for repositioning of a retraction tool back and forth along the longitudinal axis of the shaft. Flexible arm 30 offers even greater flexibility in positioning of retraction tools with respect to a surgical incision. Each of these positioning members is mated to a retraction tool by one of the preferred embodiments of the quick release attachment mechanism of present invention. Elongated shaft 28 is connected to retraction blade 32 by quick release attachment mechanism 34. Flexible arm 30 is attached to blade 36 by quick release attachment mechanism 38. Retractor blades 32 and 36 are positioned to pull the body wall 39 away from the open incision. Supporting members 28 and 30 minimize obstruction to the surgeon presented by retraction apparatus 10. Quick release attachment mechanisms 34 and 38 allow different sized and types of blades to be quickly substituted for blades 32 and 36 by the surgeon, or his or her assistant, as the incision is deepened, as different blades are needed, or if the initial selection of blades proves undesirable.

FIG. 2 illustrates an elongated shaft 42 and retractor blade 44 incorporating the elements of a quick release attachment mechanism 40 of the first preferred embodiment. Shaft 42 has an end coupling portion 46 which is seen extending through an aperture 48 in a flange 50. Flange 50 is a portion of a member 52 made of spring grade metal, attached to a face of blade 44 at end 54 by tack welds or other suitable fastening means. Spring grade metal member piece 52 includes an elongated torsion spring portion 56 disposed between end portion 54 and a flange 50. Flange 50 is bent to be substantially perpendicular to the adjacent region of blade 44. A second end portion 58 of member 52 is bent back on blade 44, spaced from the opposite face of the blade from the face to which member 50 is attached. Flange end 56 encloses aperture 48 which is sized to admit end coupling portion 46 of shaft 42.

FIG. 3 illustrates quick release attachment mechanism 40 in greater detail, with shaft 42 and blade 44 detached. End coupling portion 46 of shaft 42 includes longitudinal grooves 60 and 62 (groove 62 being shown in FIG. 4) which extend along end coupling portion 46 from lead end 66 of the shaft along opposite sides of the shaft. Spaced from lead end 66 and circumferentially girding end coupling portion 46 is a retaining groove 68. End Coupling portion 46 incorporates a tapered end portion 69 adjacent lead end 66 such that the diameter of shaft 42 is smallest at the lead end.

Retractor blade 44, within member 52, incorporates a notch 70 located approximately centered between end spring portion 54 and end portion 58. Opposite edges of notch 70 provide opposed tongues 72 and 74, each of which can dovetail into one or the other of grooves 60 or 62. As shown, the orientation of shaft 42 and blade 44 brings longitudinal groove 60 into alignment to engage tongue 72 and groove 64 into alignment to engage tongue 74. While aperture 48 is substantially aligned to admit lead end 66 of shaft 42 with grooves 60 and 62 engaging tongues 72 and 74. Actual introduction of lead end 66 results in displacement of flange end 48 in the direction indicated by arrow "A" and a resultant flexing of torsion spring 54.

Notch 70 includes an indented end portion 76. The spacing from aperture 48 to indented end portion 76 is substantially equal to the spacing from circumferential groove 68 to lead end 66 of shaft 42. Flange 50 is restrained from lateral movement in the plane of tongues 72 and 74 by shoulders 80 and 82 which extend from blade 44 around the flange in the plane of the tongues.

FIGS. 4 and 5 illustrate attachment of shaft 42 to blade 44. Pushing lead end 66 of shaft 42 into notch 70 until the terminating end abuts bottom portion 76 brings retaining groove 68 adjacent edge 78 of aperture 48. Torsion spring 54 will cause end flange 48 to move (as indicated by arrow "B" in FIG. 4) a portion of aperture edge 78 into groove 68. This results in shaft 42 being retained in notch 70. Shaft 42 and blade 44 can be detached by applying flexing force to retaining piece 50 in the direction indicated by arrow "C" (shown in FIG. 5) and pulling the shaft and blade apart. Such flexing is easily applied by grasping blade 44 and depressing retaining piece 50 by thumb or index finger.

Aperture 48 is disposed off center with respect to tongues 72 and 74 in its unflexed position. Tapered end 69 of end coupling portion 46 permits simultaneous engagement of the tongue 72 and 74 with grooves 60 and 62 of shaft 42 and insertion of coupling shaft portion 42 through aperture 48. As the shaft 42 is pushed through aperture 48, grooves 60 and 62 act against the tongues 72 and 74 to displace flange 50. When the shaft has traveled through the aperture to bring aperture edge 78 adjacent retaining groove 68, spring 56 urges flange 50 back in the opposite direction from which it has been displaced to engage aperture edge 78 with retaining groove 68. When the aperture edge 78 engages retaining groove 68, the tongues 72 and 74 provide a force against the shaft 42 so that the aperture edge 78 and the retaining groove 68 are held in positive engagement, latching shaft 42 to blade 44.

Attachment mechanism 40 provides a relatively immobilized latching between shaft 42 and retractor blade 44. Aperture edge 78 and retaining groove 68 restrain movement of shaft 42 and blade 44 longitudinally, either into or out of notch 70. Indented end portion 76 of notch 70 limits the travel of shaft 42 into the notch, and provides positive placement of the retaining groove 68 with respect to aperture 48. Tongues 72 and 74 engage longitudinal grooves 60 and 62, preventing rotation of blade 44 on the axis of shaft 42 or back on the shaft. The fit between tongues 72, 74 and aperture edge 78 with the respective grooves is preferably snug to prevent excessive play in the connection.

Attachment mechanism 10 allows essentially snap-on attachment of surgical retraction blades. Blades are aligned with the end of shafts through introduction of the shaft through a single aperture. Attachment follows pressing blade and shaft together. Release is just as easy and quick. Pressure applied to the torsion spring of the assembly releases the blade from the shaft. A wide variety of blade types and sizes can now be attached to a shaft in a retraction assembly.

Figure 6B:
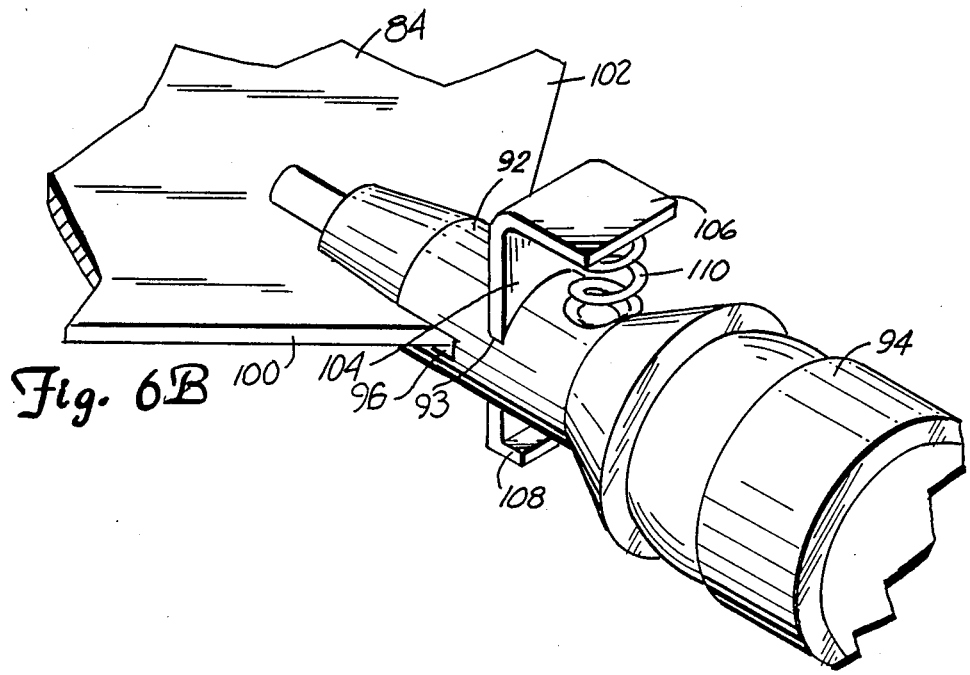
FIG. 6B is a perspective of the second embodiment in the latched state.
Figure 6A:
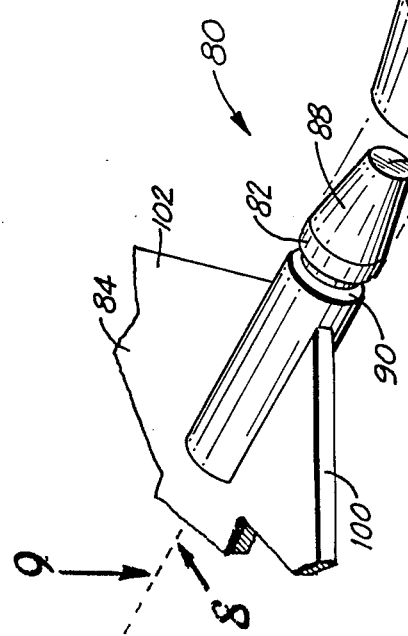
FIG. 6A is a perspective view of a second embodiment of the quick release attachment mechanism.

FIGS. 6A and 6B illustrate a second embodiment of the quick release attachment mechanism of the present invention. Attachment mechanism 80 includes a coupling shaft 82 extending from a retractor blade 84. Coupling shaft 82 has a lead end 86 and a concentrically tapered lead portion 88 adjacent the lead end. A circumferential groove 90 is disposed in coupling shaft 82 for providing a catch for the latching portion of attachment mechanism 80.

A coupling guide 92 depends from one end of a flexible arm 94 for coupling with coupling shaft 82. Coupling guide 92 includes a centered bore 95 (shown in FIG. 7) for receiving coupling shaft 82, with opposed slots 96 and 98 (slot 98 being shown in FIG. 9) extending radially from a portion of the centered bore for receiving leading edges 100 and 102 of blade 84, respectively. Extending through coupling guide 92 and intercepting centered bore 95 is a slot 93 for receiving flange 104. Extending perpendicularly to flange 104 and away from coupling shaft 82 are flange extensions 106 and 108. A compression spring 110 is fixed between flange 104 and the body of coupling guide 94, biasing the flange toward a predetermined position with respect to centered bore 95.

Figure 7:
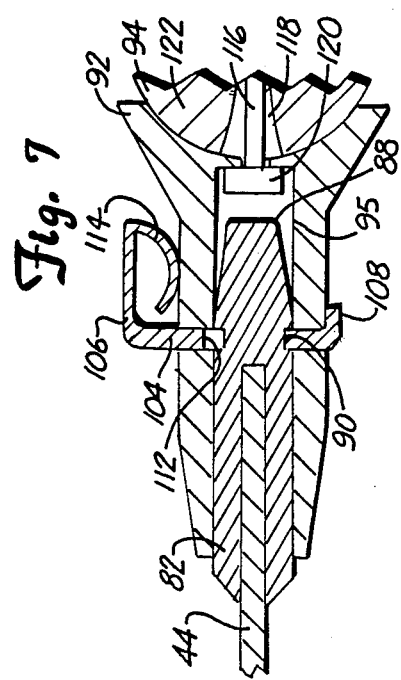
FIG. 7 is a cross-sectional view of a latched tool and positioning arm using a variation on the second embodiment of the attachment mechanism.

FIGS. 7 and 8 illustrate coupling shaft 82 introduced to centered bore 95 and latched by flange 104 into position therein. Flange 104 includes an aperture 112 through the flange and admitting coupling shaft 82 up to and including circumferential groove 90. Spring 110, or spring 114 in FIG. 7 where it is shown in alternative form as a torsional as opposed to compression spring, urges an edge of aperture 112 up into circumferential groove 90 latching coupling shaft 82 to coupling guide 92.

Flexible arm 94 includes a series of alternating concave members 124 and convex members 122 which are fitted side by side. A wire 116 is threaded through bores 118 and 126 and is anchored by a blunted end 120 in bore 95. Wire 116 can be drawn tight by mechanism not shown, and not part of the invention, to pull convex members 122 and concave members 126 tight against one another to stiffen flexible arm 94. FIG. 9 illustrates the latched coupling shaft 82 and coupling guide 92 from a top down sectional view. The relative locations of radial slots 96 and 98 for receiving leading edges 100 and 102 of tool 44 are shown.

FIGS. 10 and 11 illustrate movement of flange 104 in slot 93 to latch and release coupling shaft 82. In FIG. 10 flange latch 104 has been urged upwardly bringing an edge of aperture 112 into circumferential groove 90. Movement of flange 104 in the direction of the arrow in FIG. 10 displaces the flange to the position of FIG. 11 releasing coupling shaft 82 and allowing blade 44 to be pulled from coupling guide 94.

Although the present invention has been described with reference to preferred embodiments, workers skilled in the art will recognize that changes may be made in form and detail without departing from the spirit and scope of the invention.

What is claimed is:

1. A quick release connection mechanism for connection of a surgical retraction assembly comprising:
   an elongated coupling shaft having a lead end supported by the retraction assembly;
   a latch catch disposed on the coupling shaft spaced from the lead end of the shaft;
   longitudinally extending grooves along opposite sides of the shaft;
   a flattened portion of a surgical retraction tool;
   a slot in the flattened portion of the tool to receive the coupling shaft, the slot having facing parallel edges forming sides of the slot, for engaging the grooves along opposite sides of the shaft; and
   a latching flange disposed across and substantially perpendicular to the slot;
   an aperture through the latching flange sized to admit the coupling shaft, the aperture having a latch engaging portion, and
   a spring biasing the flange toward a position where the latch engaging portion cooperates with the latch catch to disengagedly lock the position of the coupling shaft when the coupling shaft is positioned sufficiently far enough through the latch flange aperture.

2. The quick release connection mechanism of claim 1 wherein the coupling shaft is tapered toward its lead end.

3. The quick release connection mechanism of claim 2 and further comprising:
   the latch catch comprising a circumferential groove around the coupling shaft; and
   the latch engaging portion comprising a portion of the edge of the aperture sized to fit into the circumferential groove.

4. The quick release connection mechanism of claim 3 and further comprising a flat depending from the latching flange which can be manually actuated to move latching flange to release the coupling shaft.

5. A quick release connection mechanism for connection of a surgical retraction tool to a retraction assembly, the quick release connection mechanism comprising:
   an elongated coupling shaft having a lead end and mounted to the surgical retraction tool;
   a latch catch disposed on the coupling shaft at a position spaced from the lead end of the shaft;
   guide extensions extending radially from the coupling shaft;
   a connection base attachable to the retraction assembly;
   an receiving bore in the connection base for receiving the coupling shaft;
   opposed slots extending radially from the bore for receiving the guide extensions and orienting the coupling shaft in a selected orientation;
   a flange latch extending through a slot in the connection base across the receiving bore;
   an aperture through the flange latch sized to admit the coupling shaft, edges of the aperture being adapted to cooperate with the latch catch of the coupling shaft; and
   a spring mounted between the connection base and the flange latch for biasing the flange latch toward a position where a portion of the aperture edge is inserted into the latch catch for disengagedly locking the position of the coupling shaft in the receiving bore.

6. The quick release connection mechanism of claim 5 wherein the coupling shaft is tapered toward is lead end.

7. The quick release connection mechanism of claim 6 and further comprising:
   the latch catch being a circumferential groove around the coupling shaft; and
   the edge portion of the aperture being sized to fit into the circumferential groove.

8. The quick release connection mechanism of claim 7 wherein the spring is a compression type coil spring.

9. The quick release connection mechanism of claim 7 wherein the spring is a torsion type spring.

10. Quick release connection mechanism for a retraction apparatus having a retraction tool for insertion into surgical incisions and positioning apparatus for positioning the retraction tool in surgical incisions, the quick release connection mechanism comprising:
    an elongated coupling shaft having a lead end;
    latch catch means disposed on the coupling shaft spaced from the lead end of the shaft;
    guide means adapted to cooperate with the coupling shaft orienting the shaft and for permitting movement of the shaft along a path substantially parallel to the longitudinal axis of the coupling shaft; and
    latching means including,
    a latching flange disposed cross and substantially perpendicular to the coupling shaft;

an aperture through the latching flange sized to admit the coupling shaft, the aperture having a latch engaging portion, and spring means for biasing the flange toward a position where the latch engaging portion cooperates with the latch catch means for disengagedly locking the position of the coupling shaft when the coupling shaft is positioned sufficiently far enough through the flange aperture;

the coupling shaft is tapered toward its lead end;

the latch catch means being a circumferential groove around the coupling shaft;

the latch engaging portion being an edge of the aperture sized to fit into the circumferential groove;

the latching means further comprises a flat depending from the latching flange which can be manually actuated to move latching flange to release the shaft.

11. A quick release latching mechanism between a shaft and a tool, the latching mechanism comprising:

a plurality of grooves extending longitudinally along the shaft from a first end thereof;

a latching groove disposed circumferentially around the shaft and spaced from the first end thereof;

a plurality of spaced tongues extending from the tool, disposed with respect to one another for engaging with a plurality of the longitudinally extending grooves in at least a first orientation of the tool with respect to the shaft;

a torsion spring attached to the tool; and a flange extending from the torsion spring perpendicular to the longitudinal axis of the shaft in the first orientation of the tool, the flange having an aperture sized and positioned to admit the shaft and allowing the tongues to engage the grooves, the shaft flexing the torsion spring upon admission to the aperture such that an edge of the aperture is urged into the retaining groove when the aperture and retaining groove are adjacent one another;

the shaft and tool being releasable from attachment with one another by manually flexing the torsion spring to release the edge of the aperture from the retaining groove.

12. The latching mechanism of claim 11 wherein the tool is a retractor blade.

13. The quick release attachment mechanism for retractor blades with a retractor assembly, the attachment mechanism comprising:

a shaft cooperating with the retractor assembly for positioning a selected retractor blade, the shaft having a first end thereof adapted for attachment with the selected retractor blade;

a pair of grooves extending longitudinally from the first end along opposite sides of the outside of the shaft;

a retaining groove in the shaft spaced from the first end;

a pair of tongues extending from the selected retractor blade in a plane and disposed inwardly toward one another;

a torsion spring mounted to the selected retractor blade;

a flange extending from the torsion spring through the plane of the tongues; and an aperture through the flange sized and positioned to admit the shaft with the longitudinal grooves engaging the tongues, and the torsion spring being flexed upon admission of the shaft such that an edge of the aperture is urged into engagement with the retaining groove in the shaft.

14. The attachment mechanism of claim 13 and further comprising a notch in each retractor blade, the notch having a bottom portion and opposite sides, the opposed tongues being the opposite sides of the notch.

15. The attachment mechanism of claim 14 wherein the spacing of the bottom portion of the notch from the flange corresponds to the spacing of the girding groove from the first end of the shaft such that the first end of the shaft substantially abuts against the bottom portion when a girding groove is aligned with the flange.

16. The attachment mechanism of claim 15 wherein each retractor blade further includes bracing means for preventing bending of the flange laterally on the torsion spring.

* * * * *